(12) United States Patent
Pelle Meddahi et al.

(10) Patent No.: US 9,521,839 B2
(45) Date of Patent: Dec. 20, 2016

(54) CRYOPRESERVATION OF CELLS, TISSUES AND ORGANS

(71) Applicants: INSERM (INSTITUT NATIONAL DE LA SANTE ET DE LA RECHERCHE MEDICALE), Paris (FR); UNIVERSITE PARIS DESCARTES (PARIS V), Paris (FR); UNIVERSITE DE VERSAILLES—SAINT QUENTIN EN YVELINES, Versailles (FR)

(72) Inventors: Anne Pelle Meddahi, Paris (FR); Aicha Abed, Paris (FR); Didier Letourneur, Paris (FR); Anne Baudot, Paris (FR)

(73) Assignees: INSERM (INSTITUT NATIONAL DE LA SANTE ET DE LA RECHERCHE MEDICALE), Paris (FR); UNIVERSITE PARIS DESCARTES (PARIS V), Paris (FR); UNIVERSITE DE VERSAILLES—SAINT QUENTIN EN YVELINES, Versailles (FR)

( * ) Notice: Subject to any disclaimer, the term of this patent is extended or adjusted under 35 U.S.C. 154(b) by 0 days.

(21) Appl. No.: 14/372,971

(22) PCT Filed: Jan. 17, 2013

(86) PCT No.: PCT/EP2013/050795
§ 371 (c)(1),
(2) Date: Jul. 17, 2014

(87) PCT Pub. No.: WO2013/107797
PCT Pub. Date: Jul. 25, 2013

(65) Prior Publication Data
US 2015/0087056 A1     Mar. 26, 2015

(30) Foreign Application Priority Data

Jan. 17, 2012 (EP) .................................... 12305065

(51) Int. Cl.
*A01N 1/02* (2006.01)

(52) U.S. Cl.
CPC ........... *A01N 1/0231* (2013.01); *A01N 1/0221* (2013.01); *A01N 1/0284* (2013.01)

(58) Field of Classification Search
CPC .................................................. A01N 1/0221
See application file for complete search history.

(56) References Cited

FOREIGN PATENT DOCUMENTS

| WO | WO 92/08347 | 5/1992 |
| WO | WO 94/13135 | 6/1994 |
| WO | WO 2005/053396 | 6/2005 |
| WO | WO 2009/067601 | 5/2009 |

OTHER PUBLICATIONS

Wang, et al. J of Bioactive and Compatible Polymers, 2010, 25:634-653.*
Martino et al. Biology of Reproduction, 1996, 54: 1059-1069.*

* cited by examiner

*Primary Examiner* — Bin Shen
(74) *Attorney, Agent, or Firm* — Vedder Price P.C.; Thomas J. Kowalski; Deborah L. Lu (57) ABSTRACT

The present invention provides a method for cryoprotecting a biological specimen comprising the step of freezing said biological specimen in the presence of a hydrogel and in the absence of cryoprotectant.

23 Claims, 7 Drawing Sheets

| | Tc (température de cristallisation) | q (% of crystallised solution in ice) |
|---|---|---|
| cryobeads | -16,91 | 36% |
| DMSO | -17,49 | 40% |

CRYOPRESERVATION OF CELLS, TISSUES AND ORGANS

This application is a national stage entry of international patent application Ser. No. PCT/EP2013/050795 filed Jan. 17, 2013, which published as PCT Publication No. WO/2013/107797 on Jul. 25, 2013, which claims benefit of European patent application Ser. No. 12305065.0 filed Jan. 1, 2012.

FIELD OF THE INVENTION

The present disclosure provides a method for cryopreservation of various cells, organs and tissues.

BACKGROUND OF THE INVENTION

Cryopreservation and vitrification are processes whereby biological specimen are preserved at subzero temperatures. Biological reactions are known to be slowered by lowering the temperature. However, said techniques must be performed carefully when living cells are involved. Indeed, water being the primarily component of living cells and their growth environment, the formation of ice crystal must be controlled during the freezing of said living cells in order to preserve their integrity.

It has been reported that freezing may cause damages to biological specimen, especially living cells. Indeed, during the freezing, ice crystals are formed, which have a serious deleterious effect on the cells. Intracellular crystals can damage the cell walls and structure, while the extracellular precipitation of water as ice crystals increases the salt concentrations to levels that can cause damages to the cells.

Therefore, compounds functioning as chemical or physical stabilizers, namely cryoprotective agents, have been widely used in order to protect cells against the stress encountered during freezing. The diffusion of the current classical cryoprotective agents such as dimethylsulfoxide (DMSO) into a cell will result in a partial replacement of intracellular water and help to prevent dehydration from ice formation during freezing.

However, DMSO is known to induce differentiation of some cells lines such as HT-60, ATCC CCL-240 (Collins et al., 1978). Furthermore, DMSO has been reported to expose cells, such as reproductive cells and embryos, to genetic transformation, which is unacceptable for cryopreservation.

More importantly, DMSO oxidation, which is highly rapid, induces the formation of toxic compounds. Finally, DMSO has been reported to be responsible for destabilization of phospholipid membranes (Anchordoguy et al, 2003).

Therefore, DMSO is currently highly unadapted for use in cryopreservation. Indeed, the toxicity of cryoprotective agents is a key limiting factor in cryobiology. The use of those agents thus may be manifested in the form of cryoinjuries.

There is thus a need for a cryopreservation technique, useful for various biological specimens, including cells such as reproductive cells and embryos and which does not lead to the damages related to toxicity of cryoprotectants, cryoinjury of the frozen biological specimen and/or genetic transformation of said specimen.

SUMMARY OF THE INVENTION

The inventors have shown that the use of a very specific hydrogel allows the cryopreservation of various cells and tissues, without or with a considerable decrease in classical cryoprotectants such as DMSO.

The method of the invention thus avoids the use of classical cryoprotectant, thus limiting risks of toxicity applied to the biological specimen to be cryoprotected. By avoiding or limiting the use of cryoprotectants, and therefore limiting the risk of toxicity or genetic transformation of frozen cells, the present invention provides a promising strategy of cryopreservation and vitrification.

The invention thus alleviates the technical drawbacks of the commonly used cryopreservation techniques.

DETAILED DESCRIPTION OF THE INVENTION

Definition

As used herein, the terms "cryoprotection", "cryopreservation" or "cryoconservation" refer to a process involving a freezing step whereby a biological specimen is preserved from degradation. This term encompasses conventional cryopreservation techniques as well as vitrification techniques.

As used herein, "vitrification" refers to a cryopreservation strategy where cells are converted into a glass-like amorphous solid which is free of any crystalline structure. Said process is generally achieved by a combination of high concentration of cryoprotectant and an extremely high cooling rate.

As used herein, the terms "cryoprotective agent" or "cryoprotectant" refer to an agent used to protect biological specimen from damages induced by freezing. More specifically, said agent is useful for preserving biological specimen from damages connected with ice formation within cells submitted to a freezing step. Non limiting examples of current classical cryoprotectants are dimethylsulfoxide (DMSO), ethylene glycol, polyethylene glycol (PEG), glycerol, 2-methyl-2,4-pentanediol (MPD), propanediol, sucrose, trehalose. Further examples of cryoprotectants are glucose, lactose, fructose, raffinose, propylene glycol, 1,2-/2,3 butanediol, acetamid, dextran, polymer polyvinyl alcohol, polyvinyl pyrolidone, hydroxyethyl starch, propylene glycol, 1,2-propanediol, butanediol, formamide, ficoll, mannitol, and gluconate, carboxymethylcellulose, and dextran.

As used herein, the term "polysaccharide" refers to a molecule comprising two or more monosaccharide units.

As used herein, the term "alkaline solution" refers to an aqueous solution having a pH strictly superior to 7.

As used herein, the term "aqueous solution" refers to a solution in which the main solvent is water.

As used herein, the term "cross-linking" refers to the linking of one polysaccharide chain to another one with covalent bonds.

As used herein, the terms "hydrogel" or "cryobiogel" refer to the very specific compositions obtainable by the method developed by the inventors. Said hydrogel is obtainable by chemical crosslinking of a polysaccharide such as pullulan, with a reticulating agent such as trisodium trimetaphosphate (STMP) under alkaline condition at a temperature of 50° C. Said expressions may indifferently refer to

- the hydrogel directly obtainable by crosslinking a polysaccharide with a reticulating agent, and
- the hydrogel obtainable after swelling the dried hydrogel particles.

As used herein, the term "hydrogel particles" refers to particles having different forms, like spheres, cylinders or cubes. Said hydrogel particles are thus particles of the hydrogel obtained after the grinding steps. Unless otherwise specified, the expression "hydrogel particles" are not dried.

As used herein, the expressions "dried hydrogel particle", "dried particle" and "dried cryobiogel" refer to a dried hydrogel particle having a size range lower than 5 mm, preferably lower than 1 nm, preferably lower than 50 µm, preferably lower than 25 µm. Said dried hydrogel particles are obtained by drying the hydrogel particles. Said dried hydrogel particles are swelled in an appropriate swelling solution in order to obtain a hydrogel.

As used herein, the expression "swelled hydrogel" refers to a hydrogel resulting from the swelling of dried hydrogel particles. The hydrogel directly obtained by crosslinking a polysaccharide with a reticulating agent, and the hydrogel obtainable after swelling dried hydrogel particles share the same technical and functional features.

As used herein, the expressions "dried hydrogel bead" and "dried hydrogel sphere" are used in an interchangeable manner and refer to a hydrogel particle having a substantially spherical or ovoid shape.

The invention relates to a method for cryoprotecting a biological specimen comprising the step of freezing said biological specimen in the presence of a hydrogel, wherein said hydrogel is obtainable by:
  a) chemical crosslinking of at least one polysaccharide selected from the group consisting of pullulan, dextran, dextran sulfate, scleroglucan, carboxymethyl dextran, carboxymethyl pullulan, agar, alginate, fucoidan, chitosan, hyaluronic acid, heparan-sulfate proteoglycans, heparin, heparin or heparan-sulfate mimetics, and mixtures thereof with a reticulating agent selected from the group consisting of trisodium trimetaphosphate (STMP), phosphorus oxychloride (POCl3), epichlorohydrin, formaldehydes, hydrosolubles carbodiimides and gluratealdehyde under alkaline condition at a temperature comprised between 30 and 70° C., preferably 40 and 50° C., most preferably 50° C.

Preferably, said reticulating agent is trisodium trimetaphosphate (STMP).

It is highly advantageous to use particles of the above mentioned hydrogel, especially dried hydrogel particle which may be further swells in order to restitute a hydrogel. Therefore, the particles provides an easier use because of the size of the particles which may be adapted to type and size of the cells, the tissue(s) or the organ(s) to cryopreserve. The invention therefore relates to a method for cryoprotecting a biological specimen, comprising the step of freezing said biological specimen in the presence of a hydrogel, wherein said hydrogel is obtainable by:
  a) chemical crosslinking of at least one polysaccharide selected from the group consisting of pullulan, dextran, dextran sulfate, scleroglucan, carboxymethyl dextran, carboxymethyl pullulan, agar, alginate, fucoidan, chitosan, hyaluronic acid, heparan-sulfate proteoglycans, heparin, heparin or heparan-sulfate mimetics, and mixtures thereof with a reticulating agent selected from the group consisting of trisodium trimetaphosphate (STMP), phosphorus oxychloride (POCl3), epichlorohydrin, formaldehydes, hydrosolubles carbodiimides and gluratealdehyde under alkaline condition at a temperature comprised between 30 and 70° C., preferably 40 and 50° C., most preferably 50° C.;
  b) grinding the hydrogel obtained in a) in order to obtain hydrogel particles;
  c) optionally, washing said hydrogel particles obtained in step b);
  d) optionally, sieving the hydrogel particles obtained in step b) or step c);
  e) optionally, washing the hydrogel particles obtained in step b) or step d), preferably with a saline solution, preferably phosphate buffer saline solution thoroughly rinsed in distilled water;
  f) dehydrating the hydrogel particles obtained in step b) or step e), preferably in ethanol/water baths;
  g) drying the hydrogel particles obtained in step f), preferably at 50° C. in order to obtain dried hydrogel particles;
  h) optionally, sieving the dried particles obtained in step g); and
  i) swelling the dried hydrogel particle obtained in step h) in a swelling solution to obtain a hydrogel.

As used herein, the terms "hydrogel particles" or "particles" refer to the product obtained by grinding the hydrogel according to the invention. Typically, said grinding step is operated using a Grindoxmix GM 200 knife mill with a variable speed from 2000 to 10000 rotations per minute.

Preferably, the dried hydrogel particles obtained in step g) are dried hydrogel beads.

Preferably, said freezing step is performed substantially free of or without dimethylsulfoxide (DMSO).

As used herein, "substantially free" means present in a concentration that is less than about 1%, preferably less than about 0.5%, more preferably less than about 0.1%, most preferably completely absent. Typically, "substantially free of cryoprotectant" may correspond to a quantity three times less than the quantity of cryoprotectant used in the conventional methods.

In a specific embodiment, said freezing step is performed substantially free of 1,2-propanediol, preferably with a quantity of 1,2-propanediol three time less than the quantity used in the conventional methods. Alternatively, said freezing step is performed without 1,2-propanediol.

As used herein "without" a given cryoprotectant refers to the complete absence (0%) of said cryoprotectant while carrying out the invention.

Preferably, said freezing step is performed substantially free of or without a cryoprotectant chosen among dimethylsulfoxide (DMSO), ethylene glycol, propanediol and polyethylene glycol (PEG).

Preferably, said freezing step is performed substantially free of or without a cryoprotectant chosen among dimethylsulfoxide (DMSO), ethylene glycol, polyethylene glycol (PEG), glycerol, 2-methyl-2,4-pentanediol (MPD), sucrose, and trehalose. More preferably, said freezing step is performed substantially free of or without a cryoprotectant chosen among dimethylsulfoxide (DMSO), ethylene glycol, polyethylene glycol (PEG), glycerol, 2-methyl-2,4-pentanediol (MPD), propanediol, sucrose, and trehalose.

More preferably, said freezing step is performed substantially free of or without a cryoprotectant chosen among dimethylsulfoxide (DMSO), ethylene glycol, polyethylene glycol (PEG), glycerol, 2-methyl-2,4-pentanediol (MPD), propanediol, sucrose, trehalose, glucose, lactose, fructose, raffinose, propylene glycol, 1,2-/2,3 butanediol, acetamid, dextran, polymer polyvinyl alcohol, polyvinyl pyrolidone, hydroxyethyl starch, propylene glycol, 1,2-propanediol, butanediol, formamide, ficoll, mannitol, gluconate, carboxymethylcellulose, and dextran.

More preferably, said freezing step is performed substantially free of cryoprotectant.

Typically, the freezing step is performed according to conventional techniques.

Preferably, said freezing step is performed at a temperature below 0° C. at standard pressure conditions.

Preferably, said freezing step is performed at a temperature comprised below −10° C., −20° C., −30° C., −40° C., −50° C., −60° C. preferably below −70° C. More preferably, said freezing step is performed at a temperature comprised between −70° C. and −156° C. More preferably, said freezing step is performed at a temperature of −196° C.

Preferably, said step is a mechanical refrigeration step, at a temperature comprised below −70° C., preferably at appropriate controlled cooling rate a temperature comprised between −70° C. and −156° C. Alternatively, said freezing step occurs in liquid nitrogen at a temperature of −196° C. In another embodiment, said freezing step occurs by using vitrification technology. The details of such technology fall within the general knowledge of the person skilled in the art.

Preferably, the freezing step of biological specimen occurs in the presence of a quantity of hydrogel sufficient to cryopreserve said biological tissue. The skilled person in the art would thus take care of providing a sufficient quantity of said hydrogel for carrying out efficiently the process of the invention. The skilled person of the art would also take care of providing a quantity of said hydrogel, which does not induce damages to the biological specimen.

The skilled person in the art would easily adapt the quantity of hydrogel to the right cryopreservation solution and for cryopreserving a specific and defined quantity of biological specimen. Typically, when the method of the invention implies the use of dried hydrogel particles, said quantity depends on the size of the hydrogel particles, i.e. the granolometry of such hydrogel particles.

Typically, for cryopreserving a solution containing $10^4$ to $10^6$ cells, one may use from 20 to 60 mg, preferably from 15 to 25 mg of hydrogel or hydrogel particles.

Typically, the washing step e) may be performed with a saline solution, preferably phosphate buffer saline (PBS) at a pH of 7.4. One can proceed to several washing with PBS. For example, one can wash the hydrogel:
  3 times with PBS at a concentration of 1.5M;
  2 times with PBS at a concentration of 0.15 M;
  3 times with PBS at a concentration of 0.015 M.

Each time, the hydrogel is washed thoroughly during about 20 minutes. The hydrogel is then thoroughly rinsed in distilled water for a sufficient time to obtain a hydrogel with a pH comprised between 6 and 8, preferably about 7, more preferably a pH of 7.4. Alternatively, the hydrogel may be rinsed with a continuous flow of distilled water, followed by buffer saline solution (PBS) in gradually decreasing concentrations, then dehydrated using ethanol baths of varying concentrations.

Typically, the dehydrating step is performed in ethanol/water baths. The person skilled in the art is aware of the nature and the appropriate number of said baths. For this dehydrating step, there may be several different ethanol/water baths. For example one may use
  2 baths with ethanol/PBS 0.015M at a concentration of ethanol of 70%;
  2 baths with ethanol/PBS 0.015M at a concentration of ethanol of 50%;
  1 bath with absolute ethanol.

Typically, the drying step g) may be performed at 50° C. Typically, said step is performed with the mean of a vacuum. The method of the invention may comprise a further step g') after step g) and before step h) of grinding the hydrogel particles so as to obtain a powder.

The sieving step h) leads to the formation of calibrated particles with a desired diameter. This step provides a broad range of particle size distribution. Typically, the diameter of said particles is comprised between 5 μm and 2 mm, preferably between 20 μm and 1.5 mm. Typically, said sieving step may be performed with the help of a vibratory sieve shaker. Two parameters can be adjusted on this instrument: sieve bottom acceleration, which can be set from 1.0 to 4 $m/s^2$, and variable oscillation amplitude, which goes from 0.20 to 3 mm.

The swelling step i) may be performed with different swelling solution. Said swelling solution can be any suitable medium known by the person skilled in the art. However, the inventors have evidenced that some very specific mediums provide better results when used for swelling the dried hydrogel particles.

Preferably, said swelling solution is a saline solution.

Alternatively, said swelling solution may be a commercial solution such as SCOT30, SCOT15, Perfadex, Stem, alpha solutions, Viapsan, celsior solution, UW solution, VS4 solution, Bioxell solution, Eagle medium, Hanks solution, or Dubelcco's Eagle Modified Medium.

As used herein, the expression "saline solution" or "physiological solution" refers to a solution of sodium chloride in water. Typically, said solution comprises 0.9% of sodium chloride. Typically, said solution is sterile and is isotonic, i.e. has the same osmotic pressure as blood. Therefore, said saline solution is physiological.

Preferably, said swelling solution is chosen in the group consisting of:
  i) a solution SGly, said solution comprising saline solution and glycerol, preferably at a concentration comprised between 1 and 10% of glycerol, most preferably about 5%;
  ii) a solution SGLU, said solution comprising saline solution and glucose, preferably at a concentration comprised between 5 and 20% of glucose; most preferably about 10%; and
  iii) a solution SPEG15, said solution being composed of saline solution and polyethylene glycol, preferably at a concentration of 15 g of polyethylene glycol per liter of saline solution.

As used herein, the expression "SGly" refers to a swelling solution comprising saline solution and glycerol preferably at a concentration comprised between 1 and 10% of glycerol, most preferably about 5%.

As used herein, the expression "SGLU" refers to a swelling solution comprising saline solution and glucose, preferably at a concentration comprised between 5 and 20% of glucose; most preferably about 10%.

As used herein, the expression "SPEG15" refers to a swelling solution comprising saline solution and polyethylene glycol, preferably at a concentration of 15 g of polyethylene glycol per liter of saline solution.

The quantity of the swelling solution depends on the quantity of hydrogel-particles and the nature of the biological specimen to cryopreserve. The person skilled in the art would thus easily determine the specific quantity of swelling solution in which the dried hydrogel particles would be swelled.

The method of the invention provides higher survival rates after freezing biological specimen.

In one embodiment, said biological specimen are cells such as mammalian cells, a plant cell, blood cells, reproductive cells such as oocytes or sperm cells, embryonic cells, stem cells, cells from the umbilical cord, cells of the ovarian cortex, hematopoietic progenitors or pancreatic islets. Said biological specimen may also be an embryo such as an animal embryo, human or non-human.

The inventors have shown that thanks to the very specific hydrogel of the invention, the survival rate of cryopreserved oocytes is way higher than the survival obtained with the conventional method involving the use of 1,2-propanediol (PROH), while using three times less of PROH.

In order to prevent any risk of osmotic shock when cryopreserving cells or embryos, it is preferred to inject the cells within the hydrogel. Injection of said cells within said hydrogel may be carried out according to any conventional technique. Typically, the hydrogel is placed within a cryotube, or in a high security straw in a sufficient quantity to cryopreserve the target cells. The choice of the device would depend on the nature of the cells to be cryopreserved. The cells are then injected within the hydrogel. Then, the step of freezing may occur.

In another embodiment, said biological specimen is an organ such as a heart, a lung, a skin, a vessel, a cornea, an ovary, a liver, a kidney, a pancreas, an intestine, an eye or a spleen. In this particular embodiment, it is preferred to first place the organ within only a part of the hydrogel before providing the remaining quantity of the hydrogel. Typically, before implementing the process, the person skilled in the art determines the sufficient quantity of hydrogel for cryopreserving the target organ. Then, 10 to 60%, preferably 20 to 40% of this hydrogel is placed within an adapted cryotube, straw, or pouche. Once the organ is placed within the hydrogel, the 40 to 90%, preferably 60 to 80% of the remaining hydrogel is placed inside said cryotube, straw, or pouche. Then, the step of freezing may occur.

In still another embodiment, said biological specimen are nucleic acids such as DNA or RNA. Typically, said nucleic acids are obtained by routine procedure for extracting DNA or RNA.

Typically, the dried hydrogel powder useful for carrying out the present invention has a swelling ratio comprised between 1 and 3000%. The swelling ratio of the dried hydrogel particles is determined in saline solution. Typically, the weight of dried cryobiogel is recorded ($W_d$) prior to immersion in a saline solution, preferably phosphate buffer saline (PBS). After 1 h of incubation, the excess of water is removed and the swollen cryobiogel is weighed ($W_s$). The swelling ratio is calculated according to the formula:

$$SR=[(W_s-W_d)/W_d]\times 100.$$

The dried hydrogel of the invention provides higher swelling properties than commercially available hydrogels such as Agar® or Agargel®. The dried hydrogel useful for carrying out the present invention shows unexpected results compared to any other commercial hydrogel. Said results are justified by the very specific nature of the hydrogel of the invention. It thus clearly appears that the method developed by the inventors provides very specific characteristics to said hydrogel.

When desired, the biological specimen is thawed. Typically, the thawing step is performed by placing the frozen or vitrified biological specimen into a thaw solution.

As used herein, the term "thaw" solution refers to a solution allowing the biological specimen to thaw while preserving its viability. Such medium may be any medium known in the art to be appropriate as a base medium for the particular biological specimen.

The invention relates to a method of freezing reproductive cells and/or animal embryos. As in vitro fertilization treatments are performed with fewer embryos in order to avoid multiple pregnancies, there is a need for an effective method for cryopreserving oocytes, sperm cells and embryos. The present invention is thus highly useful for cryopreserving animal (human and non human) reproductive cells and embryos.

Typically, embryos may be subjected to cryopreservation at various stages of development, preferably early stages such as morula and blastula stages.

The present invention further relates to the use of a hydrogel as a cryoprotectant, wherein said hydrogel is obtainable by:
 a) chemical crosslinking of at least one polysaccharide selected from the group consisting of pullulan, dextran, dextran sulfate, scleroglucan, carboxymethyl dextran, carboxymethyl pullulan, agar, alginate, fucoidan, chitosan, hyaluronic acid, heparan-sulfate proteoglycans, heparin, heparin or heparan-sulfate mimetics, and mixtures thereof with a reticulating agent selected from the group consisting of trisodium trimetaphosphate (STMP), phosphorus oxychloride (POCl3), epichlorohydrin, formaldehydes, hydrosolubles carbodiimides and glurataldehyde under alkaline condition at a temperature comprised between 30 and 70° C., preferably 40 and 50° C., most preferably 50° C.

The present invention further relates to the use of a hydrogel as a cryoprotectant, wherein said hydrogel is obtainable by:
 a) chemical crosslinking of at least one polysaccharide selected from the group consisting of pullulan, dextran, dextran sulfate, scleroglucan, carboxymethyl dextran, carboxymethyl pullulan, agar, alginate, fucoidan, chitosan, hyaluronic acid, heparan-sulfate proteoglycans, heparin, heparin or heparan-sulfate mimetics, and mixtures thereof with a reticulating agent selected from the group consisting of trisodium trimetaphosphate (STMP), phosphorus oxychloride (POCl3), epichlorohydrin, formaldehydes, hydrosolubles carbodiimides and glurataldehyde under alkaline condition at a temperature comprised between 30 and 70° C., preferably 40 and 50° C., most preferably 50° C.;
 b) grinding the hydrogel obtained in a) in order to obtain hydrogel particles;
 c) optionally, washing said hydrogel particles obtained in step b);
 d) optionally, sieving the hydrogel particles obtained in step b) or step c);
 e) optionally, washing the hydrogel particles obtained in step b) or step d), preferably with a saline solution, preferably phosphate buffer saline solution thoroughly rinsed in distilled water;
 f) dehydrating the hydrogel particles obtained in step b) or step e), preferably in ethanol/water baths;
 g) drying the hydrogel particles obtained in step f), preferably at 50° C. in order to obtain dried hydrogel particles;
 h) optionally, sieving the dried particles obtained in step g); and
 i) swelling the dried hydrogel particle obtained in step h) in a swelling solution to obtain a hydrogel.

All the previously mentioned technical features are applicable.

In the following, the invention will be illustrated by means of the following examples as well as the figures.

FIGURES LEGENDS

FIG. 9: Visual comparison of viscosity of the hydrogel developed by the inventors and Angargel®. After swelling, the hydrogel remained attached to the bottom of the tube when it was turned upside down, which was not the case for sold commercially gels, such as Agargel, for example, which is also used for these applications.

FIG. 12: Evaluation of the mechanical properties (Young modulii) of cryopreserved aorta. Three swelling solutions were used:
an experimental solution (SGly, 0% DMSO), and
two clinical commercial solutions (SCOT 15® and SCOT 30®, 0% DMSO, MacoPharma, France).

EXAMPLES

Example 1

Cells and Tissue Preservation

Polysaccharide based-hydrogel particles bank (Cryobiogel) was obtained by chemical crosslinking of pullulan (MW 200,000 Hayashibara, Okayama, Japan) with trisodium trimetaphosphate reticulating agent (STMP, 10% (w/w, Sigma)) under alkaline conditions at 50° C.

The resulting hydrogel was sieved on a strainer (5 mm in diameter), washed with a phosphate-buffered saline solution (PBS, pH 7.4) thoroughly rinsed in distilled water. Then, hydrogel was dehydrated in ethanol/water baths (one in 70%, two in 50% and three in absolute ethanol successively). After drying in vacuum at 50° C., the large particles were crushed and sieved to obtain calibrated hydrogel particles (ranging from 0.1 to 1.5 mm in diameter).

A) Cryobiogel Characterization
  a) Protocols
Swelling Analysis
In order to define the behavior of the hydrogel particles in a physiological environment, swelling ratios of these hydrogels were determined in physiological serum. The weights of dried cryobiogel were recorded ($W_d$) prior to immersion in PBS. After 1 h of incubation, the excess water was removed and the swollen cryobiogel was weighed ($W_e$). The swelling ratio was calculated according to the formula:

$$SR=[(W_s-W_d)/W_d]\times 100.$$

Phosphates Content
The linked phosphates content in the Cryobiogel was quantified using a phosphate assay. Briefly, 50 mg of hydrogel particles were incubated in 10% $HNO_3$ at 105° C. until complete hydrogel degradation. A solution of ammonium metavanadate ($NH_4VO_3$, 11 mmol/L) and a solution of ammonium heptamolybdate ((NH4)6Mo7O24, 43 mol/L) were then added to the degraded hydrogel solution. A calibration range was performed using a solution of 0.4 mmol/L $H_3PO_4$. Spectra of sample were recorded at 405 nm using spectrophotometer.

Thermo-Mechanical Analysis
In order to define how to use hydrogels efficiently, it is first necessary to study their thermal properties according to their composition. Actually, this systematic thermal characterization of the synthesized hydrogels will be a determining factor for their use in cryobiology.

Figure 1:
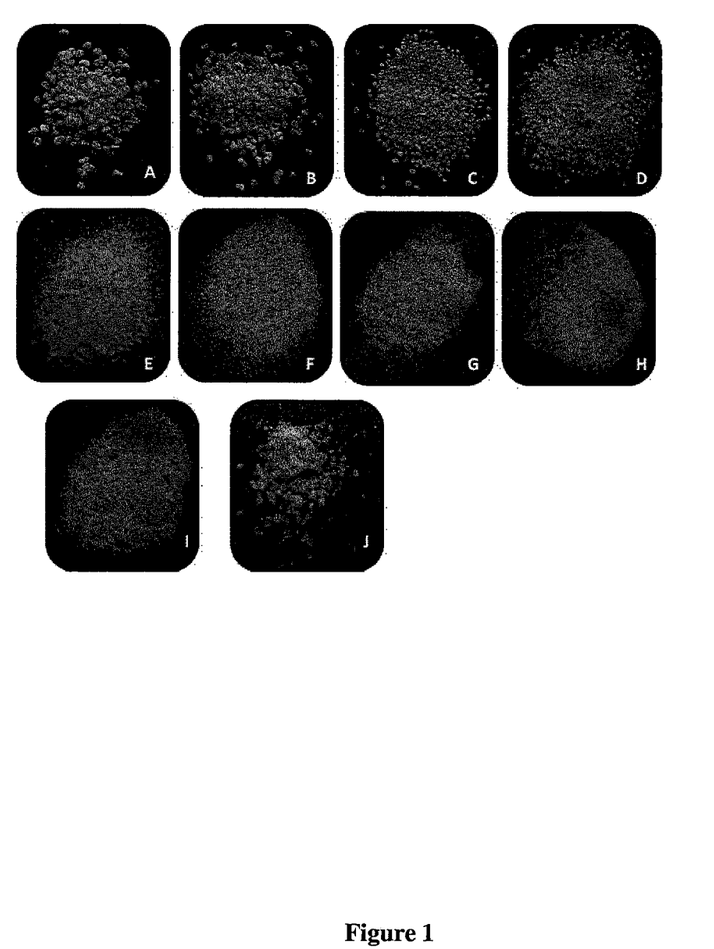
FIG. 1: Macroscopic views of the cryobiogel of various size developed by the inventors.

Differential Scanning Calorimetry
This technique, widely used in cryobiology (Boutron et al., 1979; Devireddy, 1998; Bischof, 2000), allows the observation of phase transitions under dynamic conditions on samples of a few milligrams. The corresponding glass-forming tendency and stability of the amorphous state will be so evaluated from the differential scanning calorimetric measurements. The measurements were carried out on a Setaram DSC131 thermal analyser. Sample was cool from 20° C. to −150° C. at −10° C./min. The thermograms were analysed using the thermal analysis software SETSOFT 2000.

b) Results
The hydrogel particles useful for carrying out are represented in FIG. 1. The specific characteristics of said particles are described hereafter.

Figure 2:
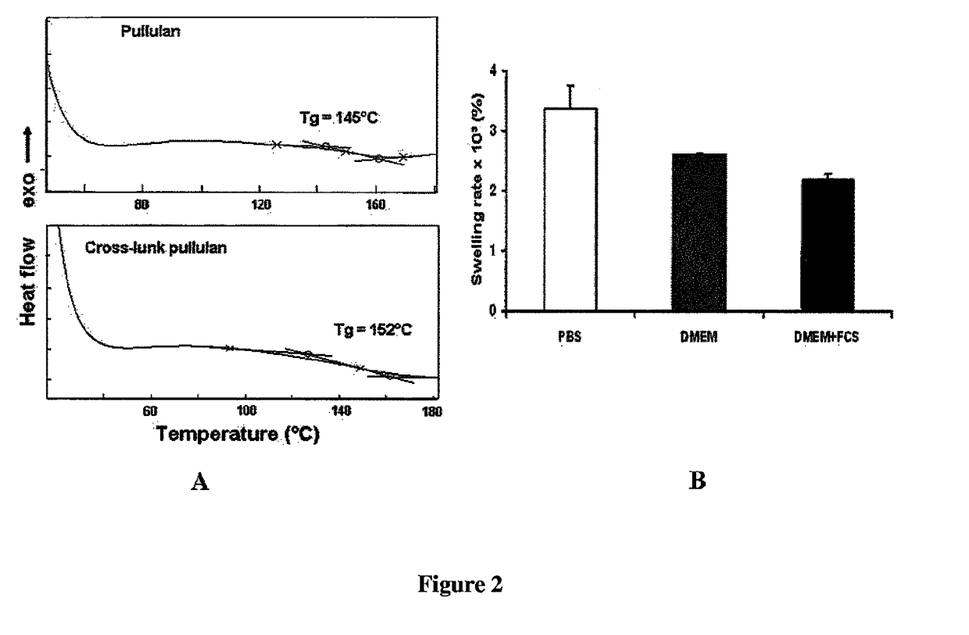
FIG. 2:
a) Thermal properties of pullulan based hydrogel. The spectra reveals a Tg variation (145° for the pullulan hydrogel and 152° for the polymerized hydrogel), making it possible to characterize the hydrogel produced.
b) Swelling rate of the dried hydrogel particles useful in the context of the invention. The swelling rate of the dried hydrogel gels is useful within the context of the invention. At room temperature for one hour, 10 mg of hydrogel was left to swell in a solution of PBS, DMEM, DMEM10% FCS. The excess liquid was removed and the hydrogel was weighed.
Figure 3:
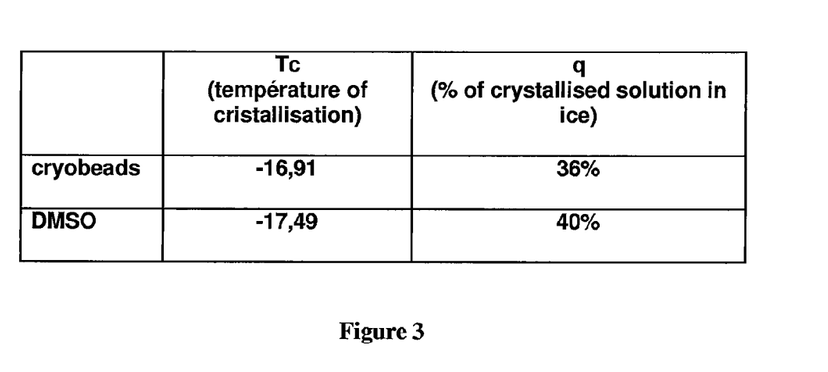
FIG. 3: Crystallisation temperature ands % of crystallised solution in ice for cryobiogel and DMSO. The figure shows the decrease in crystal ice formation when gels were used.

Swelling Rate
As shown in FIG. 2 left, the swelling rate depends on the nature of the swelling solution in which the particles are swelled.

Thermo-Mechanical Analysis
FIG. 2 right shows that characteristic of the cryobiogel useful for carrying out the method of the invention B) Preparation of Cryobiogel
Cryobiogel were swelled with 1 ml of swelling solution. Four types of swelling solution were used.
1) SGLY composed of saline solution and 5% glycerol;
2) SGLU composed of saline solution and 10% of concentrated glucose solution;

3) SPEG15 composed of saline solution and polyethylene glycol (15 g/L).

A solution of DMEM, 10% DMSO and 10% FCS was used as a control.

C) Cells Freezing and Thawing

Freezing Cells 20 mg of Cryobiogel (particle size <5 mm) were left to swell in 2 ml cryovial containing 900 µl of cryopreservation solution. 100 µL of cryopreservation solution containing 105/ml of Huvec cells (Human Umbilical Vein Endothelial Cells) or CD 34+ cells were added to the cryotube containing the swelled Cryobiogel or control medium. The cryotubes were transferred to an automatic freezer (Freezal, Air Liquide, France). The cooling rate was −1° C./min from room temperature to −80° C. or −196° C. The Cryovials were immediately transferred to a −80° C. freezer or placed in a liquid nitrogen container.

Thawing Cells

The cryovials were immersed in a water bath at 37° C. for 2 min. The cells and cryobiogels were separated with a 40 µm cell strainer (Dutscher, France) in the presence of an excess of medium. No centrifugation step was needed at this stage. For the control, cells were centrifuged at 1000 rpm for 5 minutes. Then the freezing medium was withdrawn. Cell solutions were transferred to a culture flask and incubated at 37° C. in a humidified 5% $CO^2$ atmosphere. The medium was changed every two day.

Cell Viability

Cell viability after thawing was evaluated using Trypan blue staining. Because this method cannot distinguish between necrotic and apoptotic cells, cell viability was also assessed by using the resaruzin (almarBlue) indicator dye that uses the natural reducing power of living cells to convert resazurin to the fluorescent molecule, resorufin. Viable cells continuously convert resazurin to resorufin, thereby generating a quantitative measure of viability and cytotoxicity (Al-Nasiry, S. et al. (2007). The use of alamarBlue assay for quantitative analysis of viability, migration and invasion of choriocarcinoma cells. Hum Reprod 22:1304-1309.).

Cell Culture

For cell growth experiment, HUVEC cells ($5 \times 10^3$ cells) were seeded in 24 wells plates in Dubelcco's Minimum Essential Medium (DMEM) supplemented with 10% fetal calf serum (FCS) and 2 mM L-glutamine (Sigma) at 37° C., 95% humidity, 5% $CO_2$. The medium was changed every two days. At day 1, 3 and 7, cells were harvested by trypsin-EDTA and counted with a Malassez hematocymeter. All experiments were performed at least twice and in quadruplicate samples.

D) Harvesting, Freezing and Thawing Tissue

Tissue Harvesting

Thoracic aorta were harvested from male rats (wistar, ws/ws) weighing 250 g. All procedures and animal treatment complied with the Principles of Laboratory Animal Care issued by the National Society for Medical Research (authorization no. 006235 from French Ministry of Agriculture). After general anaesthesia, the thorax wall was incised and thoracic aorta was harvested below the aortic arch and immersed in 0.9% NaCl solution (CDM Lavoisier Laboratories) before the experiment. Three segments of 1 cm were obtained from each vessel.

Tissue Freezing 60 mg of hydrogel (particle size <0.1 mm) were swelled in a 2 ml cryovial containing 1 ml of cryopreservation solution or the control medium (DMEM, 10% FCS) with Dimethylsulphoxide (Me2SO) as the cryoprotectant. Then 1 cm of aorta was placed in the cryovial. The cryotubes were transferred to an automatic freezer (Freezal, Air Liquide, France) and a cooling rate of −1° C./min was applied to reach −80° C. or −196° C. The Cryovials were immediately transferred to a −80° C. freezer or in Liquid nitrogen container.

Tissue Thawing

After storage, the cryovials were rapidly thawed by immersing in a water bath at 37° C. The cryobiogel was removed by filtration. The cryovials containing frozen samples were immersed in a water bath at 37° C. for 2 min. The tissue was removed with a forceps and immersed in saline solution to remove the hydrogel. Alternatively, an excess of medium was added and the aorta was easily recovered.

E) Evaluations of Cell and Tissue Viabilities

Cell Viability

Cell viability after thawing was evaluated by Trypan blue staining. Because this method cannot distinguish between necrotic and apoptotic cells, cell viability was also assessed by using the resaruzin (almarBlue) indicator dye that uses the natural reducing power of living cells to convert resazurin to the fluorescent molecule, resorufin. Viable cells continuously convert resazurin to resorufin, thereby generating a quantitative measure of viability and cytotoxicity (Al-Nasiry, S. et al. (2007), *The use of alamar Blue assay for quantitative analysis of viability, migration and invasion of choriocarcinoma cells*, Hum Reprod 22:1304-1309).

500 µl of cells solution ($2 \times 10^4$ cells/ml) was transferred in a well of 24 well plates with 50 µl of blue resazurin solution and incubated at 37° C. in a humidified 5% CO2 atmosphere. 4 h later resazurin reduction was measured using FluoStar Optima fluorometer and compared to reduction of cells before cryopreservation at the same concentration. The percentage of cell viability was calculated using the following formula:

percentage cell viability (%)=[(absorbance of cells after thawing)/(absorbance of cells before freeing)]×100.

The control medium was DMEM, 10% DMSO, 10% FCS for HUVEC cells or DMEM, 10% DMSO, 5% Albumin for CD34+ cells.

Cells Growth

For cell growth experiment, HUVEC cells ($5 \times 10^3$ cells) were seeded in 24 well plates in Dubelcco's Minimum Essential Medium (DMEM) supplemented with 10% fetal calf serum (FCS) and 2 mM L-glutamine (Sigma) at 37° C., 95% humidity, 5% $CO_2$. The medium was changed every two days. At day 1, 3 and 7, cells were harvested by trypsin-EDTA and counted with a Malassez hematocymeter. All experiments were performed at least twice and in quadruplicate samples.

Tissue Viability

Tissue cell viability was measured using the MIT assay. MTT (3-(4,5-Dimethylthiazol-2-yl)-2,5-diphenyltetrazolium bromide, a tetrazole) is reduced to purple formazan in the mitochondria of living cells, and this reduction takes place only when mitochondrial reductase enzymes are active. Briefly, aorta segment (1 cm) was introduced in 1 ml of MIT solution (5 mg/ml, Sigma, France) and incubated for 3 h at RT. The resulting formazan crystals were solubilized by the addition of 300 µl isopropanol for 19 h. The optical density at 570 nm was measured and the percentage cell viability was calculated using the following formula:

percentage cell viability(%)=[(absorbance of experimental aorta segment)/(absorbance of fresh aorta segment)]×100.

Results

Figure 4:
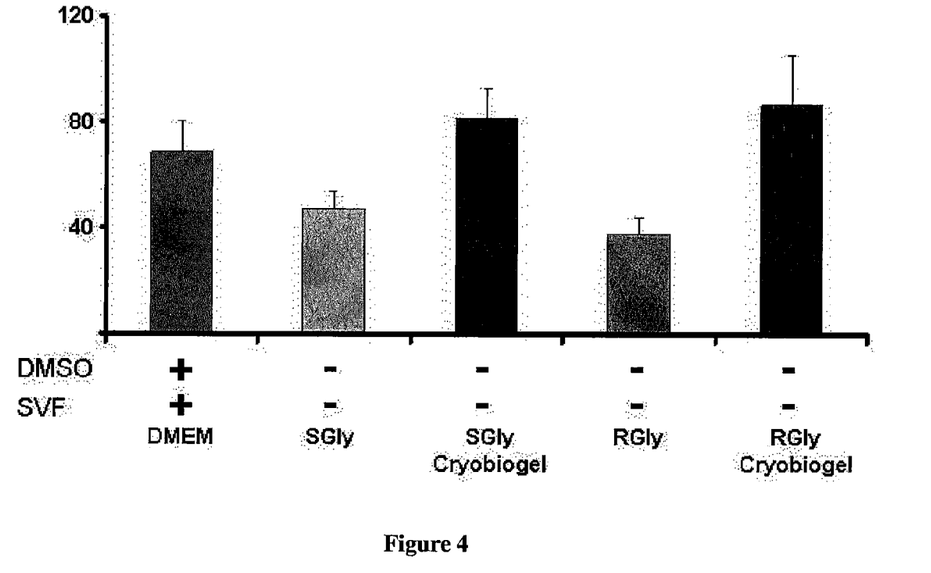
FIG. 4: Viability of HUVEC cells (Human Umbilical Vein Endothelial Cells) in various medium. The cells were frozen in the presence of gels and with no gels. The result was compared to the reference—a mixture of DMEM, 10% SVF, 10% DMSO. The figure shows that the use of the hydrogel according to the invention provides a higher percentage of cellular viability compared to the reference.

Using the protocol previously disclosed, the inventors compared the viability of HUVEC cells in various media (FIG. 4). The cryobiogel SGly and RGly provided better results even in the absence of DMSO and FCS when compared to conventional media (consisting of DMSO and SVF).

Figure 5:
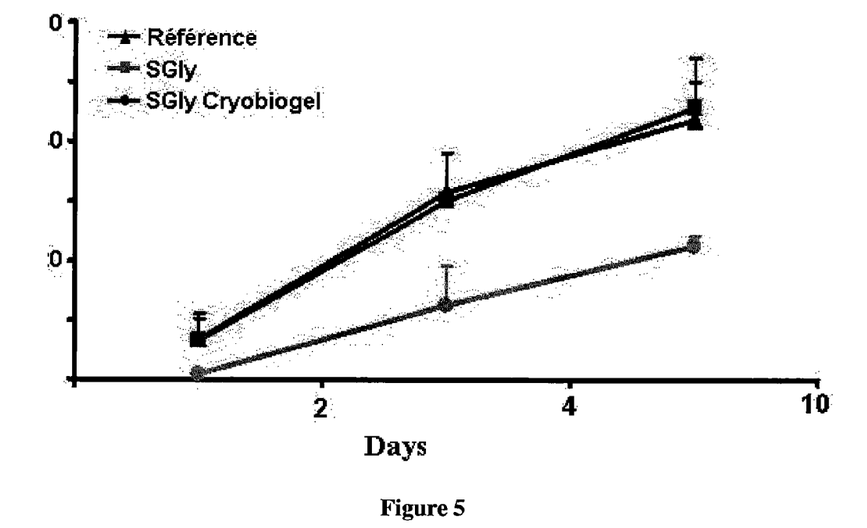
FIG. 5: Growth curb of cells after thawing. The cells were frozen with and without cryobiogel) and without DMSO or FCS (×10³/cm²) in various media: the reference, SGly, and SGly. Cell growth was identical to growth of the reference in the presence of hydrogel, despite the absence of DMSO.

FIG. 5 also shows that cell growth after thawing is improved in a cryobiogel medium when compared to a conventional SGly medium. The inventors also demonstrated that SGly Cryobiogel provide results as well as the reference medium.

Figure 6:
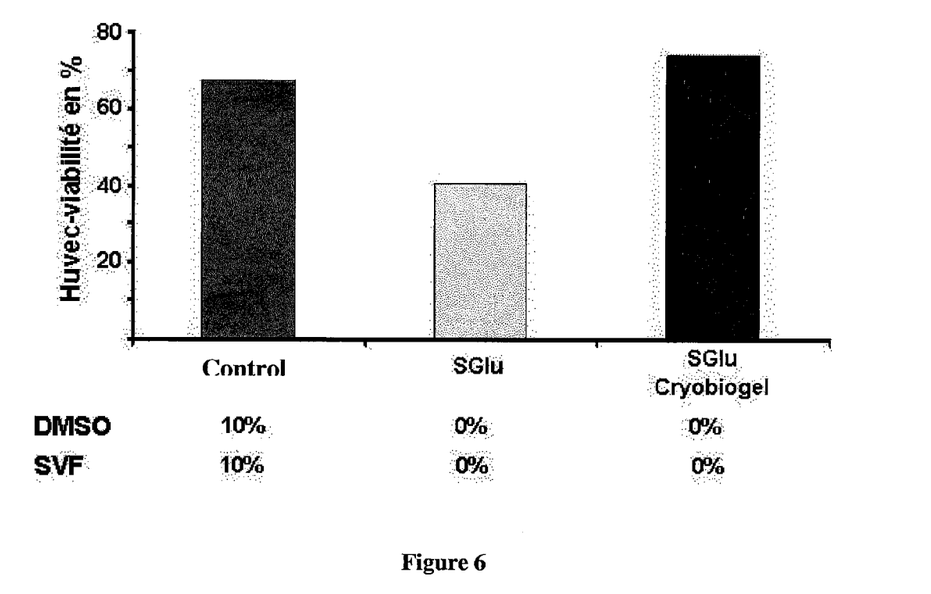
FIG. 6: Viability of HUVEC cells in various media and comparison with the standard reference for freezing (+DMSO+SVF). Cell viability was identical to that of the reference.

FIG. 6 shows that SGlu Cryobiogel provides excellent results for cryopreserving HUVEC Cells. Following slow mechanical freezing, results after thawing revealed identical cellular viability in the presence of the hydrogel when compared to the control and the reference medium.

Example 2

Aortic Vessel Cryopreservation

Arterial specimens were placed in 2 ml liquid nitrogen storage vials for cryopreservation (Nuclon-Intermed, Nunc A/S, Roskildo, Denmark) containing the cryobiogel as cryoprotectant and cryopreservative medium or containing the control medium (DMEM, 10% FCS) with Dimethylsulphoxide (Me2SO) as the cryoprotectant. Next, the arterial segments were subjected to automated controlled freezing at a gradual temperature reduction rate of 1° C./min to reach −80° C., and the segments were stored in the freezer at this temperature for a day. After this storage period, the segments were rapidly thawed by immersing in a water bath at 37° C. Excess medium was added and the aorta was easily recovered. The cryobiogel was removed by filtration.

Figure 7:
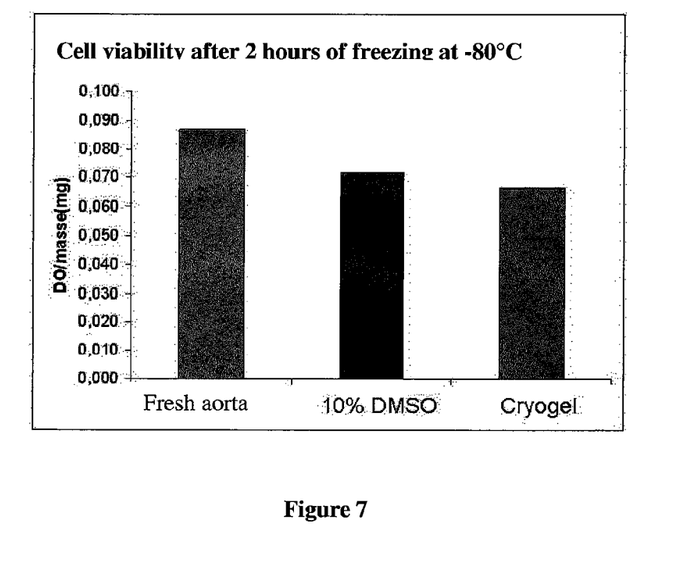
FIG. 7: Cryopreservation of aorta in different mediums as follows: 10% DMSO; and cryobiogel developed by the inventors. Results were compared to the fresh aorta. The same results were obtained with the cryobiogel in absence of DMSO.

FIG. 7 shows the cellular viability of
a) fresh aortic vessel;
b) aortic vessel in presence of DMSO;
c) aortic vessel in presence of cryobiogel; and saline solution The inventors showed that the process developed by the invention is as efficient as the conventional technique using DMSO. MTT tests provide evidence of cellular viability and proper mitochondrial function, demonstrating that this function is preserved with the hydrogel, and moreover that the findings are comparable to those observed with DMSO. The results obtained were similar to those found using a fresh aorta.

Example 3

Comparison of Swelling Properties Between the Hydrogels According to the Invention and Commercially Available Hydrogels Such as Agar® or Agargel®

The inventors showed that the hydrogel particle used in the context of the present invention is the only one offering very specific characteristic that allow it to be used in a cryopreservation process.

Figure 8:
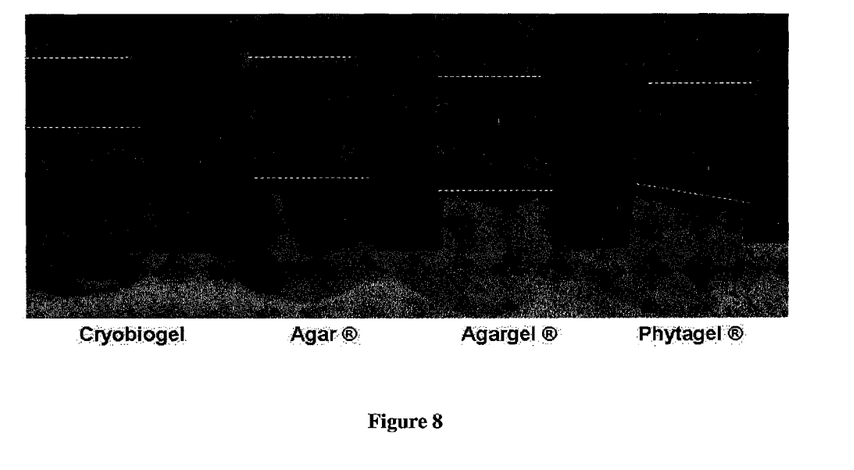
FIG. 8: Visual comparison of the hydrogel developed by the inventors and various commercially available hydrogels. For one hour at room temperature, 10 mg of each hydrogel was left to swell in physiological serum.
Figure 9:
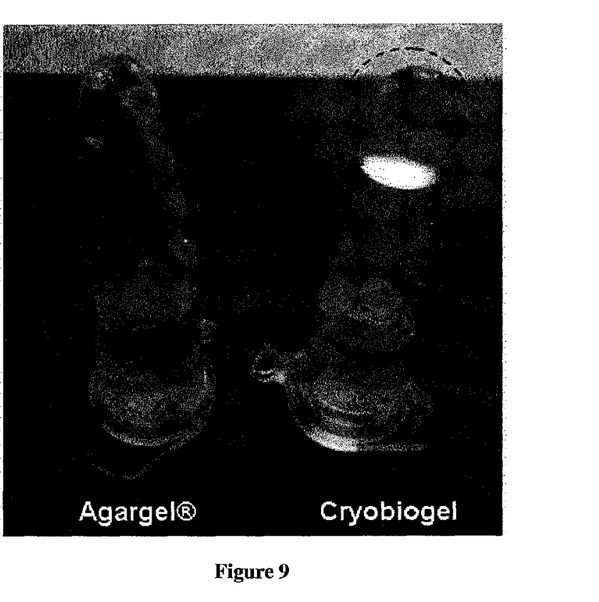

As shown in FIG. 8, the inventors compared the characteristics of the commercially available Agar®, Agargel® and Phytogel® and the hydrogel particles used in the context of the invention. After swelling, it appears that the viscosity of the hydrogel of the invention is higher, as shown in FIG. 9.

Example 4

Rabbit Embryo Freezing

Materials and Methods

Sexually mature New Zealand White doe rabbits were used (n=14). Animals were housed in flat deck cages, fed a standard pellet diet ad libitum, and had free access to water. An alternating cycle of 16 h light and 8 h dark was used.

Ovulation was induced using rhFSH (Gonal-F 75; Serono Europe Ltd., London, United Kingdom) alone or in combination with recombinant human LH (rhLH; Luveris 75; Serono Europe Ltd., London, United Kingdom), and does were inseminated. Embryos were collected 72 h after artificial insemination at compacted morula stage as previously described. Briefly, animals were anesthetized with an intramuscular injection of 0.4 mL xylazine 2% (Rompun; Bayer AG, Leverkusen, Germany) and an intravenous injection of 1.2 mL/kg body weight ketamine (Imalgene; Merial S.A., Lyon, France). Then, the abdominal region was shaved and disinfected and the ovaries and uterine horns were carefully removed before animal euthanatized. Macroscopic examination of ovaries was performed to determine the ovulation rate. Each uterine horn was flushed with 50 mL Dulbecco's phosphate-buffered saline (DPBS; Sigma, St Louis, Mo., USA) containing 0.2% bovine serum albumin (BSA; Sigma-Aldrich Quimica S.A., Madrid, Spain). The recovered flushing medium was transferred into sterile Petri dishes for examination under a stereomicroscope. Embryos were scored by morphologic criteria according to International Embryo Transfer Society classification. Only embryos in morula stage with homogeneous blastomeres and both regular mucin coat and zona pellucida were considered to be normal embryos. A total of 534 embryos were frozen.

Embryos were placed successively for 5 min into different cryopreservation mediums consisting of Embryo Holding Medium ART 019449 (Imv Technology), 4 g/L BSA and 10% DMSO (reference) or 5% DMSO (as control) or 5% DMSO and hydrogel particles (granulometry <0.5 mm; concentrations ranging from 80 mg to <20 mg). Then the embryos suspended in the cryopreservation medium were loaded into 0.25-mL sterile plastic straws (IMV, L'Aigle, France) between two drops of DPBS separated by air bubbles and sealed with a sterile plug. The straws were then placed directly into a programmable freezer (Cryologic Pty Ltd, Mulgrave, Australia) and were frozen following Menezo's two-step slow-freezing protocol. In brief, embryos were equilibrated 10 min at −7° C.; after a 5-min equilibration period, manual seeding was performed. Then, embryos were cooled to −35° C. at a freezing rate of 0.5° C./min before plunging the straws directly into liquid nitrogen. After 3 days, thawing was performed by placing the straws at room temperature for 10 to 15 sec before plunging them into a water bath at 20° C. for 1 min. After thawing, the cryopreservation medium was removed.

A total of 534 frozed-thawed embryos were cultured. Embryos were cultured for 48 h in medium TCM-199+20% fetal bovine serum (Sigma-Aldrich Quimica S.A., Madrid, Spain) at 38.5° C., 5% $CO_2$, and saturated humidity. Embryo viability and the developmental stages of thawed embryos were assessed.

Results

The results related to the in vitro viability of embryos are shown in table 1 below:

TABLE 1

Determination of in vitro viability of embryos

| MEDIUM | DEVELOPMENT TO BLASTOCYST (%) |
|---|---|
| Medium + 10% DMSO (reference) | 33.9 |
| Medium + 5% DMSO (control) | 24.9 |
| Medium + 5% DMSO + GP5_20 | 22.22 |
| Medium + 5% DMSO + GP5_60 | 20.63 |
| Medium + 5% DMSO + GP5_80 | 17.65 |
| Medium + 5% DMSO + GP1_30 | 39.66* |
| Medium + 5% DMSO + GP1_60 | 31.75* |
| Medium + 5% DMSO + GP1_80 | 32.51* |

The developmental potential of frozen-thawed embryos obtained from GP1 particle groups were similar to the reference group (Medium+10% DMSO) and significantly upper comparing to the control group (medium+5% DMSO). Addition of GP particles to medium allows a significant reduction of DMSO concentration which is interesting in clinical utilization.

No differences were observed between GP5 group and the control group. Results were correlated with the particle size and hydrogel concentration.

Example 5

Freezing Human Oocytes

The hydrogel, which was used at various concentrations, was first decontaminated with UV for 30 minutes, then swelled in the presence of 700 µL of complete DMEM culture medium (10% SVF and 1% PSA) in a 4-well plate. After the swelling of the hydrogel, the oocytes were added to each well.

These human oocytes were provided by Bichat Hospital's Medically Assisted Procreation (MAP) Laboratory. The oocyte must be loaded into a sterile, high-security plastic straw for freezing. The straws were loaded using aspiration with a 1 ml syringe having a special tip into which the plastic straw fitted. The entire apparatus is sterile and disposable (single-use). Next, freezing was carried out using NICOOL FREEZAL® (AIR LIQUIDE). This is a programmable cryogenic freezer designed for all types of sensitive biological samples: straws, tubes, bags, etc. The following freezing program was selected: 2° C./min to reach −7° C. (manual seeding), then −0.3° C./min from −7° C. to −25° C., then −25° C./min to reach −150° C. Seeding results in crystallization. After stabilization at −7° C., it is necessary to perform the seeding with a "seeding bar" (which has been immersed in liquid nitrogen) on the strew at the opposite side from the oocytes in order to initiate freezing. At the end of the freezing cycle, i.e., when the temperature has reached −150° C., the straws are removed from the Freezal using tweezers. They are put in boxes and placed in liquid nitrogen.

In order to assess the morphological appearance of the oocytes after freezing, they were observed using an optical microscope and photographed at different stages: prior to freezing, oocytes alone, then oocytes in contact with a culture medium containing the hydrogel (in C1, C2 and C3 concentrations), and after freezing.

The oocytes' morphology was routinely assessed each time they were to be handled. The first step consisted of placing the oocytes in hydrogel for 20 minutes to ensure they had not undergone osmotic shock and that they remained undamaged. A 4-well plate was used for this purpose, into which the hydrogel underwent swelling in DMEM at various concentrations (C1, C2 and C3). After 20 minutes, the oocytes were retrieved and isolated in a petri dish.

Example 6

Freezing Skin

Materials and Methods

The hydrogel-particles, which was used at various concentrations, was first decontaminated with UV for 30 minutes, then swelled in the presence of 700 µL of complete DMEM culture medium (10% SVF and 1% PSA) in a 4-well plate. After the swelling of the gel, the rat skin (6 mm diameter) was added to each well and the straws was loaded using aspiration. DMEM, 10% of dimethyl sulfoxide was used as a reference (control). Next, freezing (slow freezing or vitrification) was carried out using NICOOL FREEZAL® (AIR LIQUIDE). Samples were then placed in a liquid nitrogen tank. After one month in liquid nitrogen storage, the skin was thawed and the tissue viability was studied by MTT method as described previously.

Results

The results are summarized in Table 2 below:

TABLE 2

Determination of skin viability after freezing by MTT assay in presence of Cryobiogel or in DMSO.

| MEDIUM | DO/MG OF SKIN |
|---|---|
| +10% DMSO | 102.31 +/− 2.2 |
| +Cryobiogel, no DMSO | 90.91 +/− 3.98 |

Addition of cryobiogel to cryopreservation medium (DMEM, 10% FCS) preserve the cell tissue viability without DMSO addition and in a same proportion as the skin freezed in 10% DMSO.

Example 7

CD31 Immunostaining after HUVEC Cells Cryopreservation with Cryobiogel

In this experiment, the inventors investigated the effects of HUVEC cryopreservation with Cryobiogel on cell differentiation. This was examined by in vitro tube formation (thanks to immunofluorescence staining to identify the specific marker CD31) on Matrigel and by comparison with the method involving a solution of DMEM, 10% DMSO and 10% FCS, designated here as the gold standard method.

Matrigel was thawed at 4° C. overnight, spread evenly over each well (240 µl, 10 mg protein/ml) of 24-well plate and polymerized for more than 30 min at 37° C. Cells were thawed and then incubated in DMEM 10% FBS for 6 h and seeded onto the layer of matrigel at a density of $5 \times 10^4$ cells/well.

Figure 10:
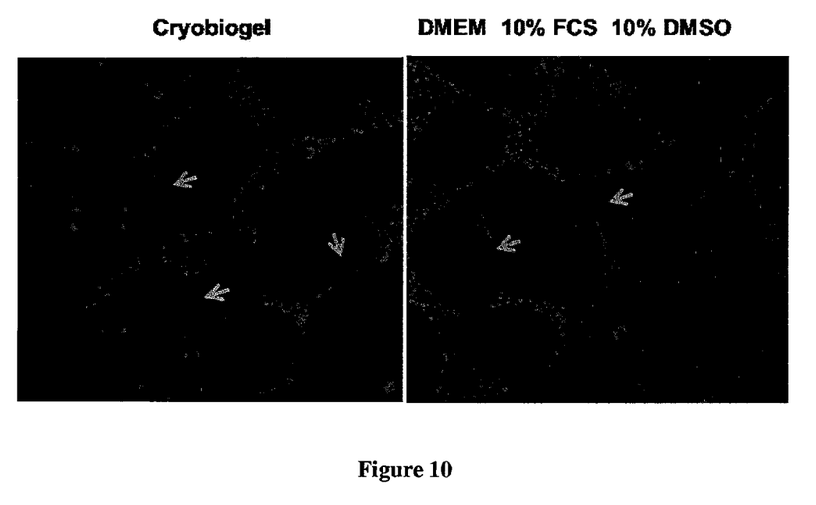
FIG. 10: Observation by immunofluorescence staining of tube formations in HUVEC cells cryopreserved with Cryobiogel or with the gold standard technique (10% DMSO, 10% FSO)

After 24 h of incubation, the tube-formation was observed (FIG. 10). Similar tube-formation was observed in HUVEC cells cryopreserved with Cryobiogel or with the gold standard technique (10% DMSO, 10% FCS).

The inventors thus showed that the Cryobiogel of the invention provides the same results that the gold standard method of prior art with regards with the ability of tissues to differentiate.

Example 8

Cryopreservation of Aortic Rat Vessel in Liquid Nitrogen

1. Effect on Tissue Organization

Aortic rat vessel structure and endothelial cell layer preservation were evaluated after one month cryopreservation in liquid nitrogen with Cryobiogel. Results were compared to the gold standard method (10% DMSO, 10% FCS).

Figure 11:
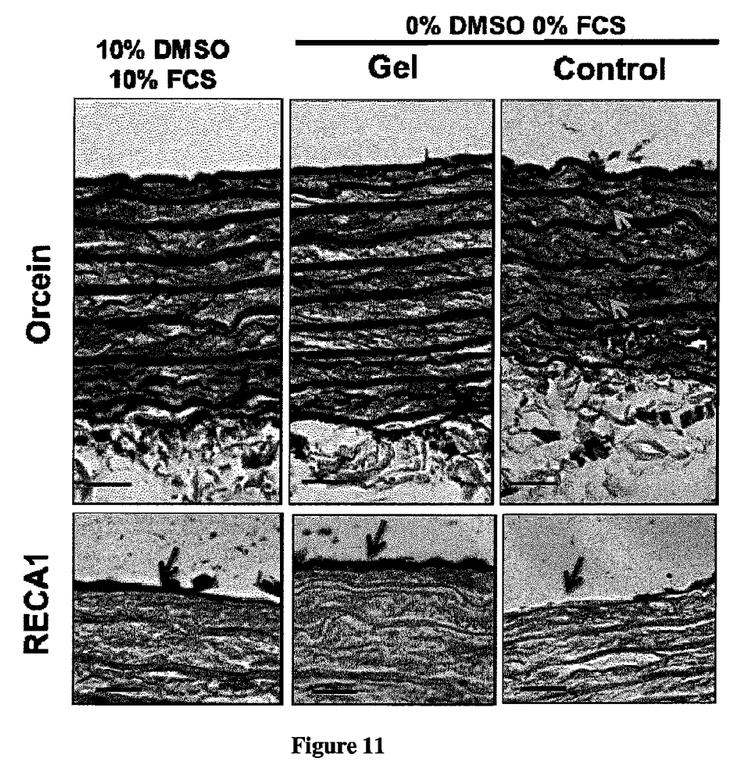
FIG. 11: Evaluation of Aortic rat vessel structure and endothelial cell layer after one month cryopreservation in liquid nitrogen with Cryobiogel and in comparison with the gold standard method (10% DMSO, 10% FCS).

As shown in the FIG. 11, no difference was observed in tissue organization between the gold standard technique and the cryobiogel.

The elastic laminas were parallels and a layer of endothelial cells were preserved (RECA1 immunostaining,). On the contrary, in the control condition (i.e. no addition of cryobiogel) a fragmentation of elastic lamina and a great space between two elastic laminas were observed (Orcein staining, yellow arrows). Furthermore, the layer of endothelial cells was absent in control conditions.

Therefore, the cryobiogel of the invention does not have any negative impact on the tissue organization of the cryopreserved cell.

2. Effect on Mechanical Properties

The inventors further investigated the mechanical properties of cryopreserved aorta in the presence of cryobiogel after one month in liquid nitrogen.

The influence of cryopreservation in the presence of cryobiogel on the aorta's mechanical properties was evaluated by tensile tests in the longitudinal direction and compared to fresh aorta and to the aorta preserved with the gold standard method (10% DMSO, 10% FCS).

Three cryopreservation solutions were used:
an experimental solution (SGly, 0% DMSO), and
two clinical commercial solutions (SCOT 15® and SCOT 30®, 0% DMSO, MacoPharma, France).

Figure 12:
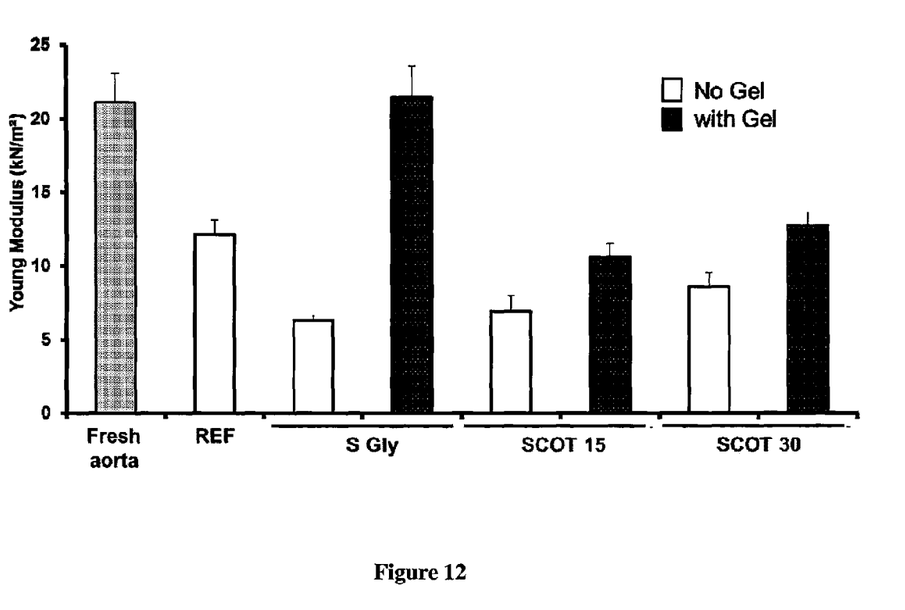

As shown in the FIG. 12, the calculated Young moduli were better with the cryopreservation in the presence of the cryobiogel compared to the control conditions and similar to the gold standard method for the SCOT solutions. The SGly solution exhibited similar results as fresh aorta.

Therefore, the cryobiogel of the invention does not have any negative impact on the mechanical properties of the cryopreserved cell. On the contrary, the method of the invention provides cryopreserved aorta exhibiting enhanced Young modulus, i.e. better mechanical properties.

Example 9

Survival of Mouse Oocytes Cryopreservation

The inventors compared the rate of oocytes survival in three different experience using 1,2-propanediol (PROH) as follows:
Group I: PROH 1.5 mol/L, Sucrose 0.3% (clinical gold standard);
Group II (control): PROH 0.5 mol/L, Albumin 10%; and
Group III: PROH 0.5 mol/L, Cryobiogel, Albumin 10%.
The results are as follows:

| | Oocytes survival (%) |
|---|---|
| Group I | 45.7 |
| Group II | 0 |
| Group III | 59.1 |

The inventors have evidenced that thanks to the very specific cryobiogel of the invention, they obtained a higher survival rate of cryopreserved oocytes while using three times less of PROH than in the conventional methods.

REFERENCES

Throughout this application, various references describe the state of the art to which this invention pertains. The disclosures of these references are hereby incorporated by reference into the present disclosure.

The invention claimed is:

1. A method for cryoprotecting a biological specimen comprising:
chemical crosslinking of at least one polysaccharide selected from the group consisting of pullulan, dextran, dextran sulfate, scleroglucan, carboxymethyl dextran, carboxymethyl pullulan, agar, alginate, fucoidan, chitosan, hyaluronic acid, heparan-sulfate proteoglycans, heparin, heparin or heparan-sulfate mimetics, and mixtures thereof with a reticulating agent selected from the group consisting of trisodium trimetaphosphate (STMP), phosphorus oxychloride ($POCl_3$), epichlorohydrin, formaldehydes, hydrosolubles carbodiimides and gluraltaldehyde under alkaline conditions at a temperature comprised between 30 and 70° C. thereby forming a hydrogel; and
freezing the biological specimen in the presence of the hydrogel at a temperature below 0° C. at standard pressure conditions, and substantially free of or without dimethylsulfoxide (DMSO).

2. The method according to claim 1, wherein said freezing step is performed at a temperature comprised below −30° C.

3. The method according to claim 1, wherein said freezing step is a mechanical refrigeration step, at a temperature comprised below −70° C., preferably at a temperature comprised between −70° C. and −156° C.

4. The method according to claim 1, wherein said freezing step occurs in liquid nitrogen at a temperature of −196° C.

5. The method according to claim 1, wherein said freezing step is performed substantially free of or without a cryoprotectant comprising dimethylsulfoxide (DMSO), ethylene glycol, or polyethylene glycol (PEG).

6. The method according to claim 1, wherein said biological specimens are mammalian cells, a plant cell, blood cells, reproductive cells, oocytes, sperm cells, embryonic cells, stem cells, cells from the umbilical cord, cells of the ovarian cortex, hematopoietic progenitors or pancreatic islets.

7. The method according to claim 1, wherein said biological specimen is an animal embryo, human or non-human.

8. The method according to claim 1, wherein said biological specimen is an organ or a tissue, a heart, a lung, a skin, a vessel, a cornea, an ovary, a liver, a kidney, a pancreas, an intestine, an eye or a spleen.

9. The method according to claim 1, wherein said biological specimen is nucleic acid, DNA or RNA.

10. A method for cryoprotecting a biological specimen comprising:
a) chemical crosslinking of at least one polysaccharide selected from the group consisting of pullulan, dextran, dextran sulfate, scleroglucan, carboxymethyl dextran, carboxymethyl pullulan, agar, alginate, fucoidan, chitosan, hyaluronic acid, heparan-sulfate proteoglycans, heparin, heparin or heparan-sulfate mimetics, and mixtures thereof with a reticulating agent selected from the group consisting of trisodium trimetaphosphate (STMP), phosphorus oxychloride ($POCl_3$), epichlorohydrin, formaldehydes, hydrosolubles carbodiimides and glurataldehyde under alkaline condition at a temperature comprised between 30 and 70° C. thereby forming a hydrogel;

b) grinding the hydrogel obtained in a) in order to obtain hydrogel particles;

c) optionally, washing said hydrogel particles obtained in step b);

d) optionally, sieving the hydrogel particles obtained in step b) or step c);

e) optionally, washing the hydrogel particles obtained in step b) or step d), preferably with a saline solution, preferably phosphate buffer saline solution thoroughly rinsed in distilled water;

f) dehydrating the hydrogel particles obtained in step b) or step e), preferably in ethanol/water baths;

g) drying the hydrogel particles obtained in step f), preferably at 50° C. in order to obtain dried hydrogel particles;

h) optionally, sieving the dried particles obtained in step g); and i) swelling the dried hydrogel particle obtained in step h) in a swelling solution to obtain a hydrogel and freezing the biological specimen in the presence of the hydrogel at a temperature below 0° C. at standard pressure conditions, and substantially free of or without dimethylsulfoxide (DMSO).

11. The method according to claim 10, wherein the temperature under alkaline conditions are at 50° C.

12. The method according to claim 10, wherein the temperature under alkaline conditions comprise between 40° C. and 50° C.

13. The method according to claim 10, wherein said freezing step is performed at a temperature comprised below −30° C.

14. The method according to claim 10, wherein said freezing step is a mechanical refrigeration step, at a temperature comprised below −70° C. preferably at a temperature comprised between −70° C. and −156° C.

15. The method according to claim 10, wherein said freezing step occurs in liquid nitrogen at a temperature of −196° C.

16. The method according to claim 10, wherein said freezing step is performed substantially free of or without a cryoprotectant comprising dimethylsulfoxide (DMSO), ethylene glycol, or polyethylene glycol (PEG).

17. The method for cryoprotecting a biological specimen according to claim 10, wherein the swelling solution in step (i) comprises:

i) a solution comprising saline solution and glycerol (SGly), preferably at a concentration comprised between 1 and 10% of glycerol, most preferably about 5%;

ii) a solution comprising physiological serum and glucose (SGLU), preferably at a concentration comprised between 5and 20% of glucose; most preferably about 10%; or iii) a solution comprising physiological saline solution and polyethylene glycol, preferably at a concentration of 15g of polyethylene glycol per liter of saline solution.

18. The method according to claim 10, wherein said biological specimens are mammalian cells, a plant cell, blood cells, reproductive cells, oocytes, sperm cells, embryonic cells, stem cells, cells from the umbilical cord, cells of the ovarian cortex, hematopoietic progenitors or pancreatic islets.

19. The method according to claim 10, wherein said biological specimen is an animal embryo, human or non-human.

20. The method according to claim 10, wherein said biological specimen is an organ or a tissue, a heart, a lung, a skin, a vessel, a cornea, an ovary, a liver, a kidney, a pancreas, an intestine, an eye or a spleen.

21. The method according to claim 10, wherein said biological specimen is nucleic acid, DNA or RNA.

22. The method according to claim 1, wherein the temperature under alkaline conditions comprise between 40° C. and 50° C.

23. The method according to claim 1, wherein the temperature under alkaline conditions are at 50° C.

\* \* \* \* \*

UNITED STATES PATENT AND TRADEMARK OFFICE
CERTIFICATE OF CORRECTION

PATENT NO. : 9,521,839 B2
APPLICATION NO. : 14/372971
DATED : December 20, 2016
INVENTOR(S) : Anne Pelle Meddahi et al.

Page 1 of 1

It is certified that error appears in the above-identified patent and that said Letters Patent is hereby corrected as shown below:

In the Claims

In Column 20, Line 17, change "between 5and 20% of glucose;" to --between 5 and 20% of glucose;--

Signed and Sealed this
Fourteenth Day of February, 2017

Michelle K. Lee
*Director of the United States Patent and Trademark Office*